United States Patent [19]
Kitagaki et al.

[11] Patent Number: 4,886,667
[45] Date of Patent: Dec. 12, 1989

[54] EXTERNAL PREPARATION COMPOSITION

[75] Inventors: Kanshiro Kitagaki; Keiko Ebihara, both of Hachioji; Shigeo Morioka, Yokohama; Takao Nakamura, Urawa; Taizo Okada, Urayasu, all of Japan

[73] Assignee: Sato Pharmaceutical Co., Ltd., Tokyo, Japan

[21] Appl. No.: 935,985

[22] Filed: Nov. 28, 1986

[30] Foreign Application Priority Data

Nov. 27, 1985 [JP] Japan .................................. 60-264993

[51] Int. Cl.$^4$ ...................... A01N 65/00; A01N 43/08
[52] U.S. Cl. .................................... 424/195.1; 514/469
[58] Field of Search ....................... 424/198.1; 514/469

[56] References Cited

PUBLICATIONS

The Dispensatory of the U.S.A., 23rd ed. 1943, p. 438.
Chem Abstract 95: 147105h 1981.
Chem Abstract 101: 97725e, 1984.

Primary Examiner—John W. Rollins
Attorney, Agent, or Firm—Sughrue, Mion, Zinn, Macpeak & Seas

[57] ABSTRACT

This invention relates to an external preparation composition containing Ratanhia extract and/or Ratanhiaphenol as a main active component for showing an antibacterial and antifungal action against pathogenic bacteria and fungi to be cause for infections skin diseases.

5 Claims, No Drawings

EXTERNAL PREPARATION COMPOSITION

FIELD OF THE INVENTION AND RELATED ART

The present invention relates to an external preparation composition, and more particularly to an external preparation composition containing Ratanhia extract and/or Ratanhiaphenol, which shows an antibacterial and antifungal action against pathogenic bacteria and fungi to be cause for infectious skin diseases.

Heretofore Ratanhia has been utilized for hemostatic and antidiarrheic drugs on the basis of its astringent action. Ratanhia is described in the official compendia of many countries, i.e. the Japanese Pharmacopoeia (3rd Revision); Deutsches Arzneibuch 8 Ausgabe; Pharmacopee Francaise 8 Eidition; Pharmacopoea Helvetica Editio Qunita, and for long period of time Ratanhia has been utilized for pharmaceuticals. There are given use patents, for example Romanian Pat. NNCZ as medicines for mouth and Dutch Pat. No. 64080 as suppositories. All these patents are based on the astringent action of tannin which is contained in Ratanhia.

On the other hand, it recently has become apparent that infectious skin diseases are mixed infectious diseases caused by aerobic bacteria and anaerobic bacteria. For example, the principal pathogenic bacteria for acne are composed of Corynebacterium acnes of anaerobic bacteria and Staphylococcus epidermidis of aerobic bacteria, and in the focus of decubitus there have been detected Bacteroides fragilis and Fusobacterium nucleatum as anaerobic bacteria and Staphylococcus aureus as aerobic bacteria.

Besides, while the principal pathogenic fungi of dermatomycosis such as epidermic ringworm, favus and tinea pedis are aerobic pathogenic fungi such as Trichophyton mentagrophytes, Trichophyton rubrum, Trichophyton canis, Microsporum gypseum and the like, as the pathogenic bacteria of secondary infectious diseases have been detected Staphylococcus aureus of aerobic bacteria, Candida albicans of aerobic yeast, and Bacteroides fragilis of anaerobic bacteria. Thus in order to product therapeutic effect for any particular infectious disease, it is also necessary to combine ingredients which have antibacterial action to both aerobic and anaerobic bacteria, and in this view point there is not always found any satisfactory external preparation. Furthermore, appearance of an ingredient has been expected which has antibacterial and antifungal action to all pathogenic bacteria of so-called infectious skin diseases from acne and decubitus to dermatomycosis and has in addition high safety.

OBJECT OF THE INVENTION

The present inventors earnestly have made research for the purpose of providing an exteral preparation which is highly safe and in addition has a wide range of antibacterial spectrum against the pathogenic bacteria which cause infectious skin diseases. Upon searching for the natural source among various plants and screening out many species they found that an external preparation combined with Ratanhia extract and/or Ratanhiaphenol which is one of ingredients in Ratanhia, have excellent antibacterial action and a wide range of antibacterial spectrum agaist the pathogenic bacteria of infectious skin diseases such as acne, decubitus dermatomycosis and the like, and then completed the present invention.

CONSTITUTION OF THE INVENTION

The present invention relates to external preparation compositions such as liquids for external use, lotions, ointments, suppositories, solid face washes, liquid face washes, creamy face washes, cataplasms, plasters and the like, with which Ratanhia extract and/or Ratanhiaphenol are combined.

The plant from which the Ratanhia extract or Ratanhiaphenol to be used in the present invention are obtained, is Ratanhia, the original plant of which is Krameria triandra Ruitz et Pavon and/or Krameria argentea Martius (Leguminosae-Caesalpinioideae). Preferably, the plant is utilized in a powder form of its root.

The Ratanhia extract is extracted from Ratanhia with a solvent such as water, ethanol, methanol, hexane, ether, acetone, ethyl acetate, toluene, benzene, propylene glycol, glycerin and the like, or a mixture thereof. Depending on the condition of the extract fraction, for example, some extract fraction is separated from the solvent by evaporation and then directly utilized as an extract having antibacterial properties, or some extract fraction is further extracted again with the afore-mentioned solvent for the purpose of increasing the content of such effective ingredient and the secondary extract fraction thus obtained is separated from the solvent, for example, by evaporation to give an extract having antibacterial properties.

Ratanhiaphenol is obtained, for example, by extracting a Ratanhia extract as mentioned above with a mixture of dilute hydrochloric acid and ethyl ether, evaporating the ether layer, then dissolving the residue in chloroform, fractionating the solution on silica gel (74 to 149μ) with chloroform and hexane 7:3 eluants to collect the Ratanhiaphenol fraction, and further recrystallizing from petroleum ether. Thus obtained Ratanhiaphenol is colorless needle-like crystals. Ratanhiaphenol thus obtained has three types of structures as shown below.

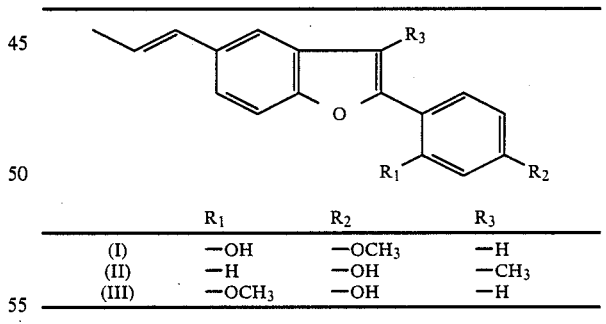

|  | $R_1$ | $R_2$ | $R_3$ |
|---|---|---|---|
| (I) | —OH | —OCH$_3$ | —H |
| (II) | —H | —OH | —CH$_3$ |
| (III) | —OCH$_3$ | —OH | —H |

Besides, as far as any Ratanhia extract or Ratanhiaphenol can be obtained, any other process other than above-mentioned extracting process constitutes no obstruct to carry out the present invention.

In the present invention may be used either a product or those products together which are obtained as Ratanhia extract or Ratanhiaphenol by such a process as mentioned above.

The amount of Ratanhia extract and/or Ratanhiaphenol to be combined with external preparation compositions ranges from 0.00005 to 5 w/w%, and preferably from 0.005 to 2 w/w%.

As other ingredients of the present invention, any ingredient suitable for the type of external preparation composition may be used. For example, when applied to a diseased part of an infectious skin disease, on considering the cases, the composition is dissolved, dispersed, or mixed in a suitable base, and furthermore, if necessary, emulsifiers, suspending agents, spreading agents, penetrating agents, keratolytics, antiphlogistics and others are added to provide medicine.

Furthermore, the external preparation compositions of the present invention also can be used in combination with antibacterial substances. Upon studying the effects of used in combination with other antibacterial substances, it has been found that when used in combination with cefalexin, novobiocin, tetracycline, nalidixic acid and tolnaftate, the external preparation compositions of the present invention showed no antagonism, but addition effect. This means that used in combination of the compositions of the present invention with other antibacterial substances does not inhibit individual antibacterial activity, and is useful to further extend the antibacterial spectrum of the compositions.

EXAMPLE 1

1. Preparation of Ratanhia extract and Ratanhiaphenol

Ratanhia extract

To 100.0 g of Ratanhia dry powder was added 500 ml of ethanol, and the mixture was heated under reflux at 60° to 70° C. for 3 hours and filtered. Then newly 250 ml of ethanol was added to the residue, and the similar reflux was repeated two times to obtain the ethanol extract from total three times of extraction. The ethanol extract was centrifuged at 12,000 rpm for 10 minutes with cooling, and the filtrate thus obtained was concentrated to dryness to give 16.2 g. The similar extractions with other solvents were carried out in the same procedure as mentioned above to obtain extracts.

In Table 1 are shown the yield (w/w%) of Ratanhia extract with each extracting solvent.

TABLE 1

| | Yield of Ratanhia extract | |
|---|---|---|
| | Extracting Solvent | Yield (w/w %) |
| A | Ethanol | 16.2 |
| B | 70 v/v % ethanol | 23.1 |
| C | Methanol | 12.6 |
| D | n-Hexane | 8.7 |
| E | Methanol + n-hexane (1:1) | 10.5 |

Ratanhiaphenol

Then the Ratanhia extract which was obtained from the liquid ethanol extract, was extracted again with a mixture of dilute hydrochloric acid and ethyl ether. The ether layer of the extract was concentrated to dryness, and the residue was dissolved in chloroform to be fractionated on silica gel (particle diameter: 74–149μ) with eluant of chloroform and n-hexane 7:3. The Ratanhiaphenol fraction was collected, which further was recrystallized to give Ratanhiaphenol crystals.

2. Antibacterial Activity (1) Antibacterial activity in vitro

The minimum inhibitory concentrations (MIC) of the Ratanhia extracts (A–E) and Ratanhiaphenol (F) which were obtained in Example 1, were determined for ten species standard 10 strains and three species clinically anaerobic 79 isolated strains. The results are respectively shown in Tables 2-1, 2-2 and 3.

Methods

MIC was determined by the agar dilution method in two time dilution.

The inoculation of bacteria was carried out with a liquid containing bacteria in $10^{6-7}$ cells/ml using a Microplanter (Sakuma Seisakusho).

In regard to cultivation condition, anaerobic bacteria were cultivated using an anaerobic box under introducing a gas mixture ($CO_2$: $H_2$: $N_2$ = 1:1:8) at 37° C. for 60 hrs in an anaerobic cultivation condition. Aerobic bacteria were cultivated at 37° C. for 48 hrs, except that pathogenic fungi were cultivated for 168 hrs, in the aerobic cultivation condition.

Strains (i) Standard strains (ATCC, RIMD, IFO)
Anaerobic bacteria:
  Bacteroides fragilis RIMD 023001
  Fusobacterium nucleatum ATCC 25586
  Corynebacterium acnes ATCC 11828
Aerobic bacteria:
  Staphylococcus aureus ATCC 6538P
  Staphylococcus epidermidis ATCC 12228
  Staphylococcus pyogenes ATCC 10389
Dermatophytes: (pathogenic fungi)
  Trichophyton mentagrophytes IFO 5466
  Trichophyton rubrum IFO 5467
  Microsporum gypseum IFO 8231
Yeast:
  Candida albicans ATCC 10261

(ii) Clinically isolated strains
Anaerobic bacteria:
  Bacteroides fragilis: 48 isolated strains
  Peptostreptococcus sp.: 22 isolated strains
  Clostridium perfringens: 9 isolated strains
Media: GAM broth medium for anaerobic bacteria, BHI medium for aerobic bacteria, and Sabouraud medium for dermatophytes and yeast were used.
Control: As antibacterial substances for control were used ticarcillin, tetracycline, cefalexin and apalcillin which are effective for anaerobic bacteria, isopropylmethylphenol which is effective for aerobic bacteria, and tolnaftate, undecylenic acid and griseofulvin which are effective for dermatophytes.

From the results of Table 2-1 and 2-2 it was apparent that combination of Ratanhia extract and/or Ratanhiaphenol provides excellent antibacterial activity against either of anaerobic bacteria, aerobic bacteria and dermatophytes.

Besides, from the results of antibacterial activity (MIC) to clinically isolated anaerobic bacteria in Table 3, Ratanhiaphenol has a small range of effective concentration in comparison with tetracycline and cefalexin, and showed 100% efficiency to 70 isolated strains of the tested bacteria at from 1.56 to 12.5 μg/ml.

To 48 isolated strains of Bacteroides fragilis, Ratanhiaphenol showed 100% efficiency at from 1.56 to 6.25 μg/ml. On the other hand, tetracycline and cefalexin showed their antibacterial action over a big range of concentration such as at from 1.56 to 400 μg/ml for tetracycline and at from 3.13 to 400 μg/ml for cefalexin.

Similarly Ratanhiaphenol showed 100% efficiency to 22 isolated strains of Peptostreptococcus sp. and 9 isolated strains of clostridium perfringens at from 3.13 to 12.5 μg/ml.

That is to say, the fact that the antibacterial action of Ratanhiaphenol is effective in a small range of concentration in comparison with the antibacterial action of tetracycline and cefalexin which is effective over a big range of concentration, shows that there are less drug resistance bacteria for Ratanhiaphenol, and therefore means that Ratanhiaphenol has an excellent antibacterial activity.

Methods of experiment:

In accordance with Kaken Method by Sakai et al. (The Japanese Journal of Medical Mycology, 1(3)252–257 (1960)), a guinea pig was depilated at 4 to 5 places of its back each in a size of 2 cm diameter with gum tapes, and abraded by a sand paper at the places. A

TABLE 2

| | Minimum inhibitory concentration to standard strains (μg/ml) | | | | | | | | | | | |
|---|---|---|---|---|---|---|---|---|---|---|---|---|
| | Present invention | | | | | | Control | | | | | |
| Strains | A | B | C | D | E | F | L | M | N | O | P | Q |
| Anaerobic bacteria | | | | | | | | | | | | |
| Bacteroides fragilis RIMD 023001 | 50 | 50 | 50 | 6.25 | 50 | 6.25 | 50 | 50 | 400 | 200 | | |
| Fusobacterium nucleatum ATCC 25586 | 50 | | | | | 6.25 | 6.25 | 12.5 | | | 200 | |
| Corynebacterium acnes ATCC 11828 | 50 | | | | | 6.25 | 50 | 25 | | | | 400 |
| Aerobic bacteria | | | | | | | | | | | | |
| Staphylococcus aureus ATCC 6538P | 3.13 | 3.13 | 3.13 | 3.13 | 3.13 | 0.39 | 3.13 | 50 | 400 | >1000 | >1000 | >1000 |
| Staphylococcus epidermidis ATCC 12228 | 3.13 | | | | | 0.39 | 6.25 | 25 | 200 | >1000 | >1000 | >1000 |
| Staphylococcus pyogenes ATCC 10389 | 6.25 | 6.25 | 6.25 | 6.25 | 6.25 | 0.10 | 6.25 | 50 | 100 | >1000 | >1000 | >1000 |
| Dermatophyte | | | | | | | | | | | | |
| Trichophyton mentagrophytes IFO 5466 | 6.25 | 6.25 | 6.25 | 6.25 | 6.25 | 1.56 | >1000 | >1000 | | 6.25 | 0.10 | 12.5 |
| Trichophyton ruburm IFO 5467 | 12.5 | | | | | 1.56 | >1000 | >1000 | | 6.25 | 0.10 | 12.5 |
| Microsporum gypseum IFO 8231 | 12.5 | | | | | 0.78 | >1000 | >1000 | | 6.25 | 0.10 | 6.25 |
| Yeast | | | | | | | | | | | | |
| Candida albicans ATCC 1026 | 50 | 50 | 50 | 12.5 | 12.5 | >10 | | | 200 | >1000 | >1000 | 200 |

A: Ethanol extract
B: 70 v/v % ethanol extract
C: methanol extract
D: n-Hexane extract
E: Methanol + n-hexane extract
F: Ratanhiaphenol
L: Ticarcillin
M: Apalcillin
N: Isopropyl-methylphenol
O: Griseofulvin
P: Tolnaftate
Q: Undecylenic acid

TABLE 3

| | | Cumulation percent of MIC of Ratanhiaphenol (%) | | | | | | | | | | | |
|---|---|---|---|---|---|---|---|---|---|---|---|---|---|
| | | MIC(μg/ml) | | | | | | | | | | | |
| Bacterium (No.) | Material | 0.1 | 0.2 | 0.39 | 0.78 | 1.56 | 3.13 | 6.25 | 12.5 | 25 | 50 | 100 | 200 | 400 |
| Bacteroides fragilis (48) | F | | | | | | 4 | 84 | 100 | | | | | |
| | R | | | | | | 19 | | 25 | 38 | 50 | 75 | 85 | 100 |
| | S | | | | | | | 4 | 8 | | 30 | 50 | 81 | 100 |
| Peptostreptococcus sp. (22) | F | | | | | | 14 | 64 | 100 | | | | | |
| | R | | | 5 | 9 | 14 | 23 | 32 | 36 | 68 | 82 | 100 | | |
| | S | | | | | | 18 | 23 | | 45 | 68 | 86 | 100 | |
| Clostidium perfringens (9) | F | | | | | | 11 | 33 | 100 | | | | | |
| | R | | | 22 | 33 | 44 | | | | 56 | 100 | | | |
| | S | | | | | | | | | 33 | 44 | 100 | | |

F: Ratanhiaphenol
R: Tetracycline
S: Cefalexin (2) Antifungal activity in vivo by trichophytosis of guinea pig.

The antifungal activity of 1% Ratanhia extract (B) and 1% Ratanhiaphenol (F) solution to experimental trichophytosis of guinea pig was examined in comparison with the positive controls of 1% clotrimazole solution and 1% thimerosal solution.

Animal used for experiment: Hartley's white male guinea pig; Body weight 400–500 g; 20 guinea pigs for one dose group.

liquid containing fungus (Trichophyton mentagrophytes IFO 5810, $1.6 \times 10^7$ spores/ml) was applied on the whole surface using a small brush. Since 2 days (48 hours) after the infection of fungus, application of the drug was continued for 8 days, one time a day and 0.1 ml a time.

One day (24 hours) after the final application of the drug, the animal was killed and 4 slices of each 0.5 cm squre were cut off from the body surface, which were transplanted on a Sabouraud agar medium (added with 400 μg/ml of cycloheximide and 50 μg/ml of chloromycetin). After cultivation for 2 weeks at 25° C., each of the slices was examined for the presence of growth of fungus.

From the number of fungal negative slices and the number of fungal negative focuses, fungal negativity index and healing index were calculated by the following formulas.

Fungal negativity index (%) =

$$\frac{\text{Number of fungal negative slices}}{\text{Number of cultivated slices}} \times 100$$

Healing index (%) = $\frac{\text{Number of fungal negative focuses}}{\text{Number of tested focuses}} \times 100$

TABLE 4

Antifungal activity to trichophytosis of guinea pig

| Drugs | Healing index (%) | Fungal negativity index (%) |
|---|---|---|
| 1% Ratanhiaphenol solution | 67 | 81 |
| 1% Ratanhia extract solution | 33 | 52 |
| 1% Clotrimazole solution | 60 | 88 |
| 1% Thimerosal solution | 100 | 100 |
| Propylen glycol solution (Ratanhia-phenol solvent) | 25 | 50 |
| No treatment | 0 | 25 |

From the results of Table 4, the healing effect of 1% Ratanhiaphenol solution was equivalent to that of 1% clotrimazole solution.

Assay:
Healing index: Fisher direct probability calculation method $p<0.05$
Fungal negativity index: $\chi^2$ assay $p<0.05$ 3. Acute toxicity Ratanhia extract (B) and Ratanhiaphenol (F) were prepared as suspension in 0.5% sodium carboxymethyl cellulose.

A single dose of each compound was administered orally or subcutaneously to ddy strain male mice, 5 weeks old.

The animals were observed frequently on the day of dosing and the daily for 16 days after dosing for any signs of toxicity or mortalities.

Then 50% lethal dose (LD50) were estimated as presents in Table 5 and 6.

All animals which survived to the end of the 16 days observation were sacrificed and examined to detect possible residual damage.

In the results no abnormal sign was observed. The toxicity of Ratanhia extract(B) and Ratanhiaphenol (F) were low.

TABLE 5

LD50 Values and mortalities in male mice after oral administration

| Drugs | Dose (g/kg) | Mortalities (Dead/Treated) | LD50 (g/kg) |
|---|---|---|---|
| Ratanhia extract | 1 | 0/5 | >5 g/kg |
|  | 5 | 0/5 |  |
| Ratanhia- | 1 | 0/5 |  |

TABLE 5-continued

LD50 Values and mortalities in male mice after oral administration

| Drugs | Dose (g/kg) | Mortalities (Dead/Treated) | LD50 (g/kg) |
|---|---|---|---|
| phenol | 5 | 2/5 | 5 g/kg |

TABLE 6

$LD_{50}$ Values and mortalities in male mice after subcutaneous administration

| Drugs | Dose (g/kg) | Mortalities (Dead/Treated) | LD50 (g/kg) |
|---|---|---|---|
| Ratanhia extract | 1 | 0/5 | >5 g/kg |
|  | 5 | 0/5 |  |
| Ratanhia-phenol | 1 | 0/5 | >5 9/kg |
|  | 5 | 0/5 |  |

EXAMPLE 2

Pharmaceutical preparation

Some examples of pharmaceuticals utilizing the external preparation compositions of the present invention are shown below.

(1) Ointments

A lipophilic ointment was prepared by the ordinary procedure according to the following formula comprising Ratanhia extract which was obtained by extraction using ethanol as extracting solvent.

|  | % |
|---|---|
| Polyoxyethylene-hardended caster oil | 1.0 |
| Polyoxyethylene lauryl ether | 2.0 |
| Diethyl sebacate | 5.0 |
| Ratanhia extract | 1.0 |
| Ethanol | 0.5 |
| Perfume | 0.1 |
| White petrolatum | Balance |
|  | 100.0% |

(2) Creamy face washes

A creamy face wash was prepared by the ordinary procedure according to the following formula comprising Ratanhiaphenol.

|  | % |
|---|---|
| Beagum | 1.0 |
| Sodium lauryl sulfate | 28.0 |
| Perfume | 0.1 |
| Diethylene glycol stearate | 2.0 |
| Ratanhiaphenol II | 0.005 |
| Cetyl alcohol | 2.0 |
| Lecithin | 2.0 |
| Water | Balance |
|  | 100.0% |

(3) Lotions

A lotion was prepared by the ordinary procedure according to the following formula comprising Ratanhiaphenol and a Ratanhia extract obtained using n-hexane as extracting solvent.

|  | % |
|---|---|
| Carboxyvinyl polymer | 0.5 |
| Cetanol | 3.0 |
| Lauromacrogol | 2.0 |
| Betaine lauryl- |  |

|  | % |
|---|---|
| dimethylaminoacetate | 3.0 |
| Ratanhia extract | 1.0 |
| Ratanhiaphenol I | 1.0 |
| Polyoxyethylene sorbitan monolaurate | 1.0 |
| Water | Balance 100.0% |

(4) Suppositories

A suppository was prepared by the ordinary procedure according to the following formula comprising a Ratanhia extract obtained using an extracting solvent consisting of methanol and n-hexane (1:1)

|  | % |
|---|---|
| Glycerol monostearate | 6.0 |
| Zinc oxide | 5.0 |
| Ethyl aminobenzoate | 3.0 |
| Ratanhia extract | 2.0 |
| Medium chain fatty acid glyceride | Balance 100.0% |

(5) Liquids

A liquid for external use was prepared by the ordinary procedure according to the following formula comprising Ratanhiaphenol.

|  | % |
|---|---|
| Diphenhydramine hydrochloride | 1.0 |
| Dipotassium glycyrrhizinate | 0.5 |
| Polyoxyethylene sorbitan monooleate | 3.0 |
| Ratanhiaphenol III | 0.1 |
| Perfume | 0.1 |
| Lauromacrogol | 0.5 |
| Water | Balance 100.0% |

(6) Plasters

A plaster was prepared by the ordinary procedure according to the followinng formula comprising a Ratanhia extract obtained using 70 v/v% ethanol as extracting solvent.

|  | % |
|---|---|
| Polyoxyethylene octyl phenyl ether | 2.0 |
| Ethanol | 0.5 |
| Rosin ester | 4.0 |
| Silicone oil | 5.0 |

|  | % |
|---|---|
| l-Menthol | 3.0 |
| Ratanhia extract | 1.5 |
| Paraffin | 5.0 |
| Sucrose fatty acid ester | 1.0 |
| Polyurethane acrylic polymer | Balance 100.0% |

What is claimed is:

1. A method of treating an infectious skin disease caused by at least one of bacteria and fungi comprising applying externally to skin of a patient in need thereof a pharmaceutical preparation comprising an antibacterial or antifungal effective amount of at least one of ratanhia extract and ratanhiaphenol in combination with at least one pharmaceutically acceptable additive.

2. A method according to claim 1 wherein said preparation comprises ratanhiaphenol which is selected from the group consisting of formulas (I), (II) and (III):

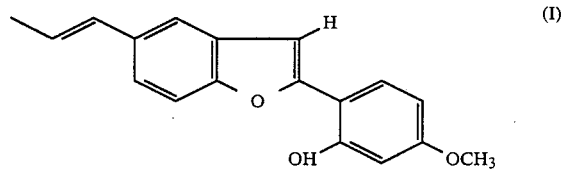

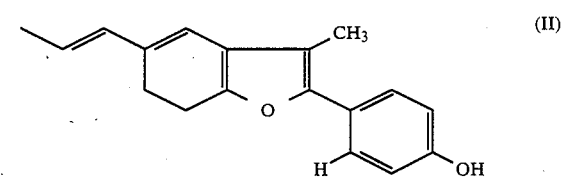

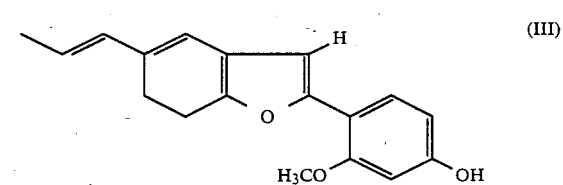

3. A method according to claim 1 wherein said at least one of ratanhia extract and ratanhiaphenol is present in said preparation in an amount from 0.00005-5 w/w% based upon the total weight of said preparation.

4. A method according to claim 3 wherein said amount is from 0.0005-2 w/w%.

5. A method according to claim 1 wherein said additive comprises a solvent for said ratanhia extract and ratanhiaphenol and is selected from the group consisting of water, ethanol, methanol, hexane, ether, acetone, ethyl acetate, toluene, benzene, propylene glycol, glycerin and mixtures thereof.

* * * * *